(12) United States Patent
Zhang

(10) Patent No.: US 11,504,065 B2
(45) Date of Patent: Nov. 22, 2022

(54) SIGNAL CONVERSION CIRCUIT, HEART RATE SENSOR AND ELECTRONIC DEVICE

(71) Applicant: SHENZHEN GOODIX TECHNOLOGY CO., LTD., Shenzhen (CN)

(72) Inventor: Mengwen Zhang, Shenzhen (CN)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 1019 days.

(21) Appl. No.: 16/214,069

(22) Filed: Dec. 8, 2018

(65) Prior Publication Data

US 2019/0117166 A1 Apr. 25, 2019

Related U.S. Application Data

(63) Continuation of application No. PCT/CN2017/106919, filed on Oct. 19, 2017.

(51) Int. Cl.
| | |
|---|---|
| *A61B 5/00* | (2006.01) |
| *H03F 3/45* | (2006.01) |
| *H03F 3/08* | (2006.01) |
| *H03F 3/00* | (2006.01) |
| *A61B 5/024* | (2006.01) |

(52) U.S. Cl.
CPC ........ *A61B 5/7203* (2013.01); *A61B 5/02416* (2013.01); *H03F 3/005* (2013.01); *H03F 3/082* (2013.01); *H03F 3/45192* (2013.01); *H03F 3/45273* (2013.01); *H03F 2203/45156* (2013.01); *H03F 2203/45326* (2013.01); *H03F 2203/45551* (2013.01)

(58) Field of Classification Search
None
See application file for complete search history.

(56) References Cited

U.S. PATENT DOCUMENTS

| | | | |
|---|---|---|---|
| 5,410,145 A | 4/1995 | Coroy | |
| 5,795,300 A | 8/1998 | Bryars | |
| (Continued) | | | |

FOREIGN PATENT DOCUMENTS

| | | |
|---|---|---|
| CN | 1543060 A | 11/2004 |
| CN | 103119866 A | 5/2013 |
| (Continued) | | |

*Primary Examiner* — Patricia J Park

(57) ABSTRACT

A signal conversion circuit, a heart rate sensor, and an electronic device are provided, and the signal conversion circuit includes: a photoelectric conversion circuit, configured to convert an optical signal into a current signal; a differential signal conversion circuit, connected to the photoelectric conversion circuit, and configured to convert the current signal into a first differential signal and a second differential signal, where the first differential signal is an integration signal of the current signal in a first phase, and the second differential signal is an integration signal of the current signal in a second phase; and a subtraction amplifier, connected to the differential signal conversion circuit, and configured to amplify a difference value between the first differential signal and the second differential signal, to generate a third differential signal. The signal conversion circuit of embodiments of the present disclosure can effectively suppress ambient interference.

18 Claims, 3 Drawing Sheets

(56) References Cited

U.S. PATENT DOCUMENTS

| | | |
|---|---|---|
| 6,781,468 B1 | 8/2004 | Robinson et al. |
| 8,283,620 B2 | 10/2012 | Raynor et al. |
| 8,692,200 B2 | 4/2014 | Tao et al. |
| 2010/0052741 A1 | 3/2010 | Venkataraman et al. |
| 2010/0065720 A1* | 3/2010 | Raynor .................. H03F 3/087 |
| | | 250/201.1 |
| 2011/0163233 A1 | 7/2011 | Ng et al. |
| 2016/0022160 A1* | 1/2016 | Pi ....................... A61B 5/02416 |
| | | 600/479 |
| 2016/0050026 A1 | 2/2016 | Hidri et al. |

FOREIGN PATENT DOCUMENTS

| | | |
|---|---|---|
| CN | 104739386 A | 7/2015 |
| CN | 106333667 A | 1/2017 |
| CN | 106535753 A | 3/2017 |
| WO | 2017166463 A1 | 10/2017 |

\* cited by examiner

SIGNAL CONVERSION CIRCUIT, HEART RATE SENSOR AND ELECTRONIC DEVICE

CROSS-REFERENCE TO RELATED APPLICATIONS

The present application is a continuation of international application No. PCT/CN2017/106919, filed on Oct. 19, 2017, of which is incorporated herein by reference in its entirety.

TECHNICAL FIELD

Embodiments of the present disclosure relate to the field of electronic technologies, and in particular, to a signal conversion circuit, a heart rate sensor, and an electronic device.

BACKGROUND

A current-type sensor has a very high output impedance, and in order to effectively convert a current signal into a voltage signal, a current-voltage (I-V) conversion circuit is generally employed. However, since a conversion circuit has a very low input impedance, an ambient interference signal may easily enter the I-V conversion circuit. For example, in a heart rate acquisition system, a human body and a circuit are not the same equipotential body, and therefore, noise on human skin is transmitted to an input end of the I-V circuit through a medium such as air, and then converted into a noise voltage by the I-V conversion circuit, so that a signal-to-noise ratio (SNR) of the entire acquisition system decreases dramatically.

In the prior art, a method of resolving this problem is to increase a distance between the human body and the circuit, so as to weaken a coupled path, however this causes the signal to decrease as the distance increases, and therefore, when a certain distance is reached, the SNR begins to decrease again; another method is to add a shielding case to the current-type sensor, however this leads to a decrease in light transmittance. In addition, the current-type sensor with an additional shielding case is likely to generate a parasitic capacitor, which causes the noise of the I-V circuit to-be amplified again.

That is, a signal conversion circuit capable of effectively suppressing ambient interference does not exist in the prior art.

SUMMARY

A signal conversion circuit, a heart rate sensor, and an electronic device are provided. The signal conversion circuit can effectively suppress ambient interference.

In a first aspect, provided is a signal conversion circuit, including:

a photoelectric conversion circuit, configured to convert an optical signal into a current signal, where the current signal in a first phase includes a signal converted from a useful optical signal, a modulated optical signal and a background optical signal in the optical signal, and the current signal in a second phase includes a signal converted from the background optical signal;

a differential signal conversion circuit 200, connected to the photoelectric conversion circuit 100, and configured to convert the current signal into a first differential signal and a second differential signal, where the first differential signal is an integration signal of the current signal in the first phase, and the second differential signal is an integration signal of the current signal in the second phase; and a subtraction amplifier 300, connected to the differential signal conversion circuit 200, and configured to subtract the second differential signal from the first differential signal and amplify an obtained difference value, to generate a third differential signal.

In an embodiment of the present disclosure, common mode noise introduced from the ambient can be suppressed through the differential signal conversion circuit 200. Specifically, for the differential signal conversion circuit 200, the current signal is a differential mode quantity, and an external interference signal is a common mode quantity. That is, the differential signal conversion circuit 200 merely allows the current signal of the photoelectric conversion circuit to pass through, and coupled interference is suppressed.

In some possible implementation manners, the differential signal conversion circuit 200 includes: a first differential signal generation circuit configured to integrate the current signal in the first phase; and a second differential signal generation circuit configured to integrate the current signal in the second phase, where the first differential signal generation circuit is connected in parallel with the second differential signal generation circuit.

In some possible implementation manners, the first differential signal generation circuit includes a first integration circuit 210 and a second integration circuit 220, the second differential signal generation circuit includes a third integration circuit 230 and a fourth integration circuit 240, each of integration circuits includes a capacitor and a switch, and the differential signal conversion circuit 200 further includes: a first switch 251, a second switch 252 and a first transconductance amplifier 290, one end of the photoelectric conversion circuit 100 is connected to a positive input end of the first transconductance amplifier 290 through the first switch 251, and the other end of the photoelectric conversion circuit 100 is connected to a negative input end of the first transconductance amplifier 290 through the second switch 252, the positive input end of the first transconductance amplifier 290 is connected to a negative output end of the first transconductance amplifier 290 through the first integration circuit 210, the negative input end of the first transconductance amplifier 290 is connected to a positive output end of the first transconductance amplifier 290 through the second integration circuit 220, the third integration circuit 230 is connected in parallel with the first integration circuit 210, and the fourth integration circuit 240 is connected in parallel with the second integration circuit 220.

When both the first switch 251 and the second switch 252 are turned on, the first integration circuit 210 and the second integration circuit 220 are configured to integrate the current signal in the first phase, and the third integration circuit 230 and the fourth integration circuit 240 are configured to integrate the current signal in the second phase.

In some possible implementation manners, the photoelectric conversion circuit 100 is a photodiode, the first transconductance amplifier 290 is configured to receive a first voltage, and the first voltage is used for adjusting a reverse bias voltage of the photodiode.

According to the technical solution of the embodiment of the disclosure, a signal to noise ratio can be further improved.

In some possible implementation manners, the differential signal conversion circuit 200 includes: a negative feedback loop configured to cancel a signal remaining in the background optical signal when the differential signal conversion circuit 200 converts the current signal into the first differential signal and the second differential signal.

In some possible implementation manners, the negative feedback loop includes: a third switch 253, a fourth switch 254 and a current sampling circuit 270, the first integration circuit 210 is connected to the negative output end of the first transconductance amplifier 290 through the third switch 253, the second integration circuit 220 is connected to the positive output end of the first transconductance amplifier 290 through the fourth switch 254, and the positive output end of the first transconductance amplifier 290 is connected to the negative output end of the first transconductance amplifier 290 through the current sampling circuit 270.

When both the third switch 253 and the fourth switch 254 are turned off, the current sampling circuit 270 is configured to detect the signal remaining in the background optical signal; and when both the third switch 253 and the fourth switch 254 are turned on, the current sampling circuit 270 is configured to cancel the signal remaining in the background optical signal.

According to a technical solution of an embodiment of the present disclosure, a dynamic range of a valid signal input by the differential signal conversion circuit 200 can be increased.

In some possible implementation manners, the current sampling circuit 270 includes: a fifth switch 261, a sixth switch 263, a seventh switch 268, an eighth switch 260, a first capacitor 264, a second capacitor 267, a first metal-oxide-semiconductor MOS transistor, a second MOS transistor 265, a third MOS transistor 266 and a fourth MOS transistor 269; the positive output end of the first transconductance amplifier 290 is connected to a drain electrode of the first MOS transistor 262 through the fifth switch 261, the drain electrode of the first MOS transistor 262 is connected to a gate electrode of the first MOS transistor 262, the gate electrode of the first MOS transistor 262 is connected to a gate electrode of the second MOS transistor 265 through the sixth switch 263, a source electrode of the first MOS transistor 262 is connected to a source electrode of the second MOS transistor 265, the gate electrode of the second MOS transistor 265 is connected to the source electrode of the second MOS transistor 265 through the first capacitor 264, a drain electrode of the second MOS transistor 265 is connected to a drain electrode of the third MOS transistor 266 through the photoelectric conversion circuit 100, a gate electrode of the third MOS transistor 266 is connected to a source electrode of the third MOS transistor 266 through the second capacitor 267, the gate electrode of the third MOS transistor 266 is connected to a gate electrode of the fourth MOS transistor 269 through the seventh switch 268, the source electrode of the third MOS transistor 266 is connected to a source electrode of the fourth MOS transistor 269, the gate electrode of the fourth MOS transistor 269 is connected to a drain electrode of the fourth MOS transistor 269, and the drain electrode of the fourth MOS transistor 269 is connected to the negative output end of the first transconductance amplifier 290 through the eighth switch 260; where the first MOS transistor 262 and the second MOS transistor 265 are "N-type" MOS transistors, and the third MOS transistor 266 and the fourth MOS transistor 269 are "P-type" MOS transistors.

In some possible implementation manners, when the fifth switch 261, the sixth switch 263, the seventh switch 268 and the eighth switch 260 are all turned on, the current sampling circuit 270 is configured to detect the signal remaining in the background optical signal; and when the fifth switch 261, the sixth switch 263, the seventh switch 268 and the eighth switch 260 are all turned off, the current sampling circuit 270 is configured to cancel the signal remaining in the background optical signal.

In some possible implementation manners, the differential signal conversion circuit 200 further includes: a second transconductance amplifier 280, a positive input end of the second transconductance amplifier 280 is connected to the positive input end of the first transconductance amplifier 290, a negative input end of the second transconductance amplifier 280 receives a common mode voltage, and the common mode voltage is used for stabilizing a voltage value of the positive input end of the first transconductance amplifier 290.

According to a technical solution of an embodiment of the present disclosure, the differential signal conversion circuit 200 can be ensured to be in a normal operating state through the second transconductance amplifier 280.

In some possible implementation manners, the subtraction amplifier 300 includes: a first branch 310, a second branch 320, a third branch 330, a fourth branch 340 and a third transconductance amplifier 370, where the first branch 310 and the second branch 320 are configured to receive the first differential signal, the third branch 330 and the fourth branch 340 are configured to receive the second differential signal, and the third transconductance amplifier 370 is configured to generate the third differential signal according to the first differential signal and the second differential signal.

In a second aspect, provided is a heart rate sensor including: the signal conversion circuit according to any one of the first aspects.

In some possible implementation manners, the heart rate sensor further includes:

an analog to digital converter, connected to the signal conversion circuit, and configured to convert an analog signal output by the signal conversion circuit into a digital signal.

In a third aspect, provided is an electronic device including: the heart rate sensor of any one of the possible implementation manners in the second aspect.

In some possible implementation manners, the electronic device may be a smart wearable device such as an earphone or a wristband.

DETAILED DESCRIPTION

Technical solutions in embodiments of the present disclosure will be described hereinafter in conjunction with the accompanying drawings.

It should be understood that a signal conversion circuit of an embodiment of the present disclosure can be applied to any apparatus and device configured with a signal conversion circuit. In particular, the technical solution of the embodiment of the present disclosure is applicable to a weak current signal amplification front end that is sensitive to ambient noise, and an application with a special requirement for an anti-interference capability and a high SNR. For example, a heart rate sensor.

In order to suppress ambient interference, the present disclosure provides a signal conversion circuit with a new structure, so that an influence of the ambient interference is suppressed.

Figure 1:
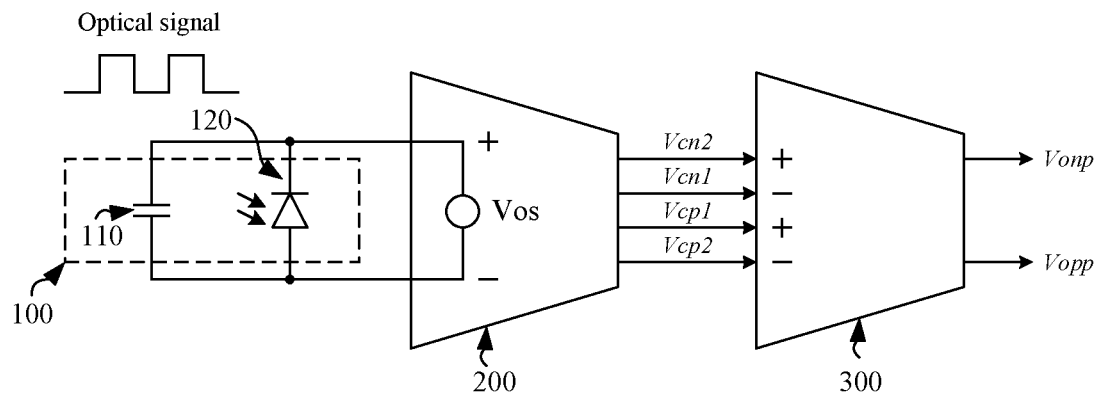
FIG. 1 is a schematic block diagram of a signal conversion circuit of an embodiment of the present disclosure.

FIG. 1 is a schematic block diagram of a signal conversion circuit of an embodiment of the present disclosure.

As shown in FIG. 1, the signal conversion circuit includes a photoelectric conversion circuit 100, configured to convert an optical signal into a current signal, where the current signal in a first phase includes a signal converted from a useful optical signal, a modulated optical signal and a background optical signal in the optical signal, and the current signal in a second phase includes a signal converted from the background optical signal; a differential signal conversion circuit 200, connected to the photoelectric conversion circuit 100, and configured to convert the current signal into a first differential signal and a second differential signal, where the first differential signal is an integration signal of the current signal in the first phase, and the second differential signal is an integration signal of the current signal in the second phase; and a subtraction amplifier 300, connected to the differential signal conversion circuit 200, and configured to amplify a difference value between the first differential signal and the second differential signal, to generate a third differential signal.

The useful optical signal in the embodiment of the present disclosure may be an optical signal carrying target information (for example, heart rate data information), and the modulated optical signal may be a modulated signal for modulating the useful optical signal, and the background optical signal may be a signal formed by ambient light received by the photoelectric conversion circuit 100. In other words, an input signal of the photoelectric conversion circuit 100 in the embodiment of the present disclosure includes the useful optical signal, the modulated optical signal, and the background optical signal. It should be understood that definitions of the useful optical signal, the modulated optical signal, and the background optical signal are exemplary, and the embodiment of the present disclosure is not specifically limited.

In addition, the first phase and the second phase in the embodiment of the present disclosure are different phases, and the embodiment of the present disclosure does not specifically limit meanings of the first phase and the second phase. For example, the first phase may refer to: all phases included in a converted current signal when the photoelectric conversion circuit 100 is configured to convert the useful optical signal, the modulated optical signal, and the background optical signal in the optical signal into a current signal; and the second phase may refer to all phases included in a converted current signal when the photoelectric conversion circuit 100 is configured to merely convert the background optical signal in the optical signal into a current signal.

Since the photoelectric conversion circuit 100 has a very high output impedance, in order to effectively convert the current signal into a voltage signal, in the embodiment of the present disclosure, common mode noise introduced from ambient may be suppressed through the differential signal conversion circuit 200.

Figure 2:
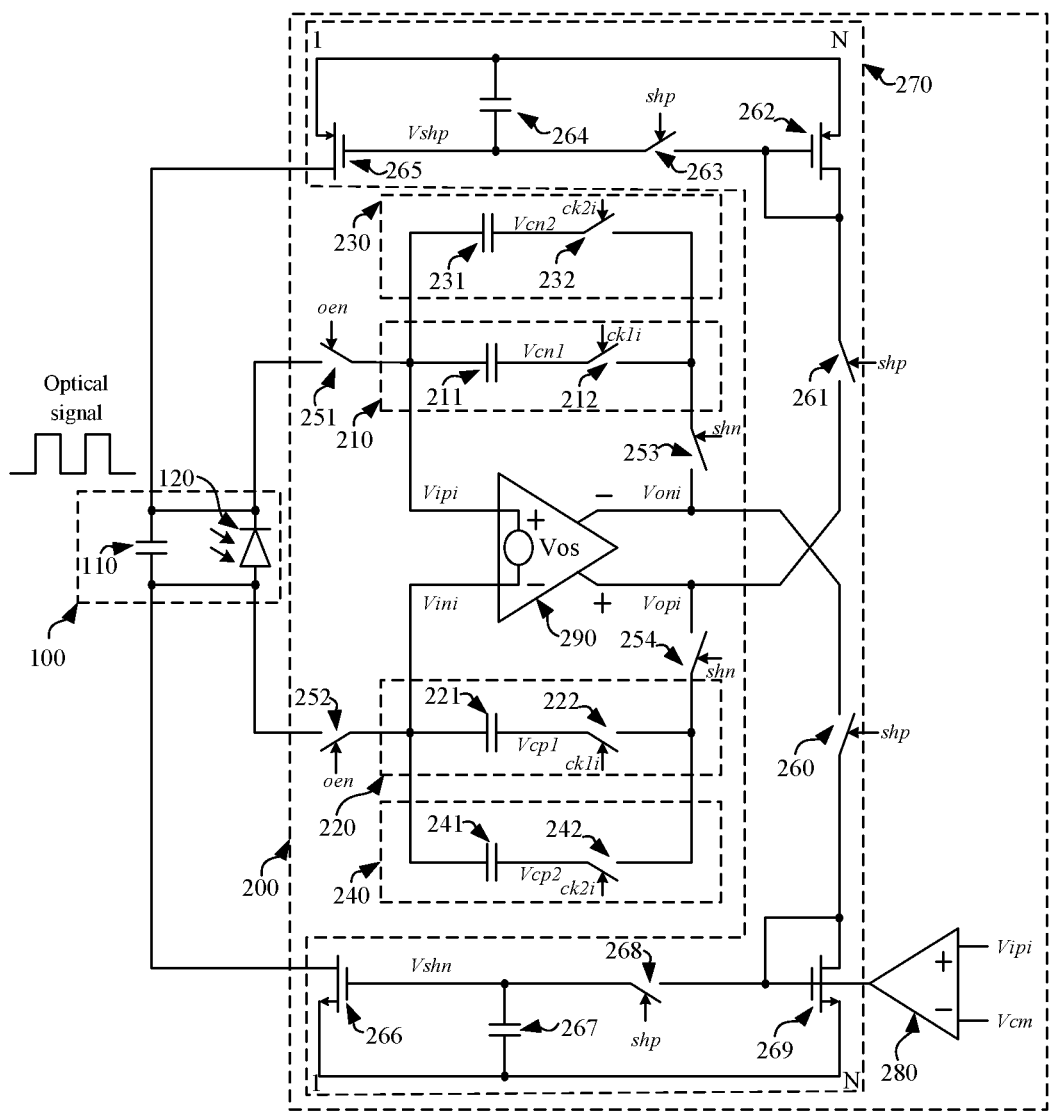
FIG. 2 is a schematic diagram of a signal conversion circuit of an embodiment of the present disclosure.

Specifically, as shown in FIG. 2, the current signal flows in from one end of the photoelectric conversion circuit 100, and flows out from the other end of the photoelectric conversion circuit 100. Therefore, for an input of the differential signal conversion circuit 200, the current signal is a differential mode quantity. It is assumed that an external interference signal is coupled to both Vipi and Vini, the interference signal is a common mode quantity. The differential signal conversion circuit 200 merely allows a current of the photoelectric conversion circuit to flow through. That is, coupled interference is suppressed.

That is, the differential signal conversion circuit 200 in the embodiment of the present disclosure can effectively suppress an ambient interference signal, thereby improving a signal-to-noise ratio of an output signal.

Further, for an entire conversion process from the photoelectric conversion circuit 100 to the differential signal conversion circuit 200 and then to the subtraction amplifier 300, when receiving the current signal output by the photoelectric conversion circuit, the differential signal conversion circuit 200 suppresses the common mode noise introduced from the ambient, and then respectively integrates the current signals in the first phase and the second phase thereby obtaining the first differential signal and the second differential signal.

The first differential signal is the integration signal of the current signal in the first phase, and the second differential signal is the integration signal of the current signal in the second phase; and the current signal in the first phase includes the signal converted from the useful optical signal, the modulated optical signal and the background optical signal, and the current signal in the second phase includes the signal merely converted from the background optical signal.

Therefore, if the foregoing background optical signal is a constant quantity, the subtraction amplifier 300 may amplify the difference value between the first differential signal and the second differential signal, so that the differential signal output by the subtraction amplifier 300 does not involve the background optical signal, thereby further improving the signal-to-noise ratio.

In short, first, the photoelectric conversion circuit 100 generates the current signal, and then the differential signal conversion circuit 200 acquires an integrated differential mode quantity of the current signal in two phases (that is, the first differential signal and the second differential signal). Finally, the differential signals in the two phases are subtracted by the subtraction amplifier 300, and thus the signal-to-noise ratio of the output signal is increased.

It should be noted that in the embodiment of the present disclosure, the background optical signal is different from the common mode noise introduced from the ambient.

The background optical signal refers to a signal formed through collection of background light by the photoelectric conversion circuit 100, and the background light here may be understood as the signal formed through the collection of light (for example, ambient light) which is not emitted by a LED light source, by the photoelectric conversion circuit 100. The common mode noise refers to a noise signal that is not generated by the photoelectric conversion circuit 100 and is input to the differential signal conversion circuit 200, for example, noise on human skin in a heart rate acquisition system, or the like.

Therefore, the signal conversion circuit of the embodiment of the present disclosure can not only suppress the common mode noise introduced from the ambient through the differential signal conversion circuit 200, improve the signal-to-noise ratio of the output signal, but also make it possible that the differential signal output by the subtraction amplifier 300 does not involve the background optical signal (when the background optical signal is a constant quantity), to further improve the signal-to-noise ratio, thereby improving accuracy of signal detection.

Optionally, the photoelectric conversion circuit 100 may be a photodiode.

Specifically, as shown in FIG. 1, the photoelectric conversion circuit 100 includes a diode 120 and a parasitic capacitor 110, and the diode 120 is connected in parallel with the parasitic capacitor 110. The diode 120 may be an ideal diode, that is, a diode with a forward voltage drop of zero and a reverse leakage current of zero.

It should be understood that the photodiode is merely used as an exemplary description of the photoelectric conversion circuit 100, which is not specifically limited in the embodiment of the present disclosure. For example, the differential signal conversion circuit 200 may also integrate a weak current signal from other devices.

A differential signal conversion circuit 200 of an embodiment of the present disclosure will be described by way of example.

Optionally, the differential signal conversion circuit 200 includes: a first differential signal generation circuit configured to integrate the current signal in the first phase; and a second differential signal generation circuit configured to integrate the current signal in the second phase, where the first differential signal generation circuit is connected in parallel with the second differential signal generation circuit.

FIG. 2 is a schematic diagram of a differential signal conversion circuit 200 of an embodiment of the present disclosure.

As shown in FIG. 2, the first differential signal generation circuit includes a first integration circuit 210 and a second integration circuit 220, the second differential signal generation circuit includes a third integration circuit 230 and a fourth integration circuit 240, each of integration circuits includes a capacitor and a switch, and the differential signal conversion circuit 200 further includes: a first switch 251, a second switch 252 and a first transconductance amplifier 290, one end of the photoelectric conversion circuit 100 is connected to a positive input end of the first transconductance amplifier 290 through the first switch 251, and the other end of the photoelectric conversion circuit 100 is connected to a negative input end of the first transconductance amplifier 290 through the second switch 252, the positive input end of the first transconductance amplifier 290 is connected to a negative output end of the first transconductance amplifier 290 through the first integration circuit 210, the negative input end of the first transconductance amplifier 290 is connected to a positive output end of the first transconductance amplifier 290 through the second integration circuit 220, the third integration circuit 230 is connected in parallel with the first integration circuit 210, and the fourth integration circuit 240 is connected in parallel with the second integration circuit 220.

When both the first switch 251 and the second switch 252 are turned on, the first integration circuit 210 and the second integration circuit 220 are configured to integrate the current signal in the first phase, and the third integration circuit 230 and the fourth integration circuit 240 are configured to integrate the current signal in the second phase.

Specifically, as shown in FIG. 2, the first integration circuit 210 includes a third capacitor 211 and a ninth switch 212, the second integration circuit 220 includes a fourth capacitor 221 and a tenth switch 222, the third integration circuit 230 includes a fifth capacitor 231 and an eleventh switch 232, and the fourth integration circuit 240 includes a sixth capacitor 241 and a twelfth switch 242. The ninth switch 212 in the first integration circuit 210 and the tenth switch 222 in the second integration circuit 220 may be controlled to be turned on or turned off through a first control signal (ck1$i$), and the eleventh switch 232 in the third integration circuit 230 and the twelfth switch 242 in the fourth integration circuit 240 may be controlled to be turned on or turned off through a second control signal (ck2$i$).

More specifically, when the first control signal ck1$i$=1 (at a high level), the ninth switch 212 and the tenth switch 222 are turned on, and when the first control signal ck1$i$=0 (at a low level), the ninth switch 212 and the tenth switch 222 are turned off. Similarly, when the second control signal ck2$i$=1 (at a high level), the eleventh switch 232 and the twelfth switch 242 are turned on, and when the second control signal ck2$i$=0 (at a low level), the eleventh switch 232 and the twelfth switch 242 are turned off.

Figure 5:
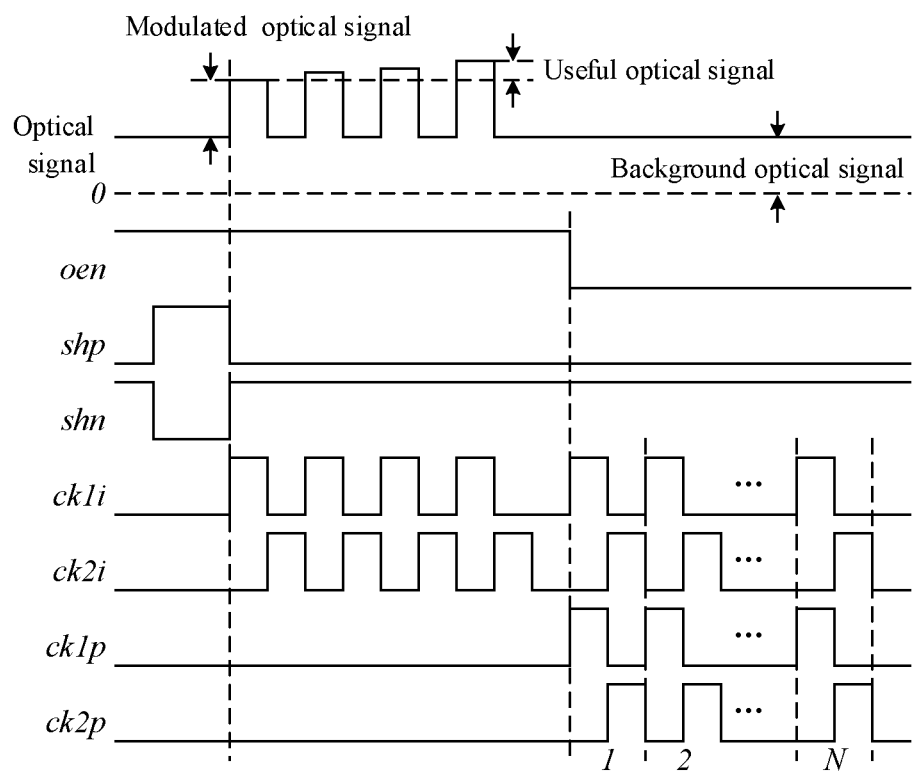
FIG. 5 is a schematic diagram of an operation timing of a signal conversion circuit of an embodiment of the present disclosure.

As shown in FIG. 5, in a process of an actual operation of the differential signal conversion circuit 200, the first switch 251 and the second switch 252 are turned on. When ck1$i$=1 and ck2$i$=0, the ninth switch 212 and the tenth switch 222 are turned on, the eleventh switch 232 and the twelfth switch 242 are turned off, and the first integration circuit 210 and the second integration circuit 220 are configured to integrate the current signal in the first phase. When ck1$i$=0 and ck2$i$=1, the ninth switch 212 and the tenth switch 222 are turned off, the eleventh switch 232 and the twelfth switch 242 are turned on, and the third integration circuit 230 and the fourth integration circuit 240 are configured to integrate the current signal in the second phase.

In other words, when ck1$i$=1 and ck2$i$=0, the ninth switch 212 and the tenth switch 222 are turned on, the eleventh switch 232 and the twelfth switch 242 are turned off, and the third capacitor 211 and the fourth capacitor 221 integrate the inputted modulated optical signal, useful optical signal and background optical signal; and when ck1$i$=0 and ck2$i$=1, the ninth switch 212 and the tenth switch 222 are turned off, the eleventh switch 232 and the twelfth switch 242 are turned on, and the fifth capacitor 231 and the sixth capacitor 241 integrate the inputted background optical signal.

It should be noted that, assuming that the background optical signal is a constant quantity, it is not difficult to see that the difference between integrated differential mode quantities of the current signals in the two phases is an integration quantity of the useful optical signal and the modulated optical signal, and in the embodiment of the disclosure, such conversion is accomplished through the subtraction amplifier 300. Specifically, when integration is completed by the differential signal conversion circuit 200, the first switch 251 and the second switch 252 are turned off; that is, an output of the photoelectric conversion circuit 100 no longer affects the integrator.

Optionally, the photoelectric conversion circuit 100 is a photodiode, the first transconductance amplifier 290 is also configured to receive a first voltage, and the first voltage is used for adjusting a reverse bias voltage of the photodiode.

Specifically, as shown in FIG. 2, a greater parasitic capacitance of the parasitic capacitor (Cpd) 110 may cause noise of the first transconductance amplifier 290 itself to be amplified. Cpd may be divided into a diffusion capacitance and a barrier capacitance, and since the photodiode is reverse biased, the diffusion capacitance may be basically ignored. It can be found that since barrier capacitance is inversely proportional to a voltage of the photodiode. Therefore, it needs to increase the reverse bias voltage of the photodiode as much as possible in order to obtain lower noise.

In the embodiment of the present disclosure, as shown in FIG. 2, the positive input end Vipi and the negative end Vini of the differential signal conversion circuit 200 are respectively connected to a cathode and an anode of the photodiode, and at this time, by inputting a first voltage Vos to the first transconductance amplifier 290, the photodiode may be biased to an appropriate reverse bias voltage, thereby reducing the Cpd and further improving the signal-to-noise ratio of the output signal of the differential signal conversion circuit 200.

In addition, since the current signal in the embodiment of the present disclosure includes the signal converted from the background optical signal, when the background optical signal is not a constant quantity, a dynamic range of a valid signal input by the differential signal conversion circuit 200 may be reduced. In other words, it is possible that the valid signal (that is, the valid signal input by the subtraction amplifier 300) output by the differential signal conversion circuit 200 includes the foregoing signal remaining in the background optical signal.

For example, assuming that the background optical signal is a constant quantity, it can be considered that the first differential signal is a differential signal formed through integration of the modulated optical signal and the useful optical signal in the first phase by the differential signal conversion circuit 200, and the second differential signal is zero.

However, assuming that the background optical signal is a floating variable, it can be considered that the first differential signal is a differential signal formed through integration of the signal remaining in the background optical signal, the modulated optical signal and the useful optical signal of the current signal in the first phase by the differential signal conversion circuit 200, and the second differential signal is a differential signal formed through integration of the signal remaining in the background optical signal of the current signal in the second phase by the differential signal conversion circuit 200.

The signal remaining in the background optical signal referred to herein may refer to: the signal obtained by subtracting a constant quantity from the background optical signal, a differential mode quantity, and an optical signal that may be integrated by the differential signal conversion circuit 200 in the background optical signal.

Therefore, in the embodiment of the present disclosure, a negative feedback loop is also provided, a dynamic range of a valid signal input by the differential signal conversion circuit 200 could be increased by canceling the signal remaining in the background optical signal.

Optionally, the differential signal conversion circuit 200 includes: a negative feedback loop configured to cancel a signal remaining in the background optical signal when the differential signal conversion circuit 200 converts the current signal into the first differential signal and the second differential signal.

For example, as shown in FIG. 2, the negative feedback loop includes: a third switch 253, a fourth switch 254 and a current sampling circuit 270, the first integration circuit 210 is connected to the negative output end of the first transconductance amplifier 290 through the third switch 253, the second integration circuit 220 is connected to the positive output end of the first transconductance amplifier 290 through the fourth switch 254, and the positive output end of the first transconductance amplifier 290 is connected to the negative output end of the first transconductance amplifier 290 through the current sampling circuit 270; where when both the third switch 253 and the fourth switch 254 are turned off, the current sampling circuit 270 is configured to detect the signal remaining in the background optical signal; and when both the third switch 253 and the fourth switch 254 are turned on, the current sampling circuit 270 is configured to cancel the signal remaining in the background optical signal.

For example, as shown in FIG. 2, the current sampling circuit 270 includes: a fifth switch 261, a sixth switch 263, a seventh switch 268, an eighth switch 260, a first capacitor 264, a second capacitor 267, a first metal-oxide-semiconductor (Metal-Oxide-Semiconductor, MOS) transistor 262, a second MOS transistor 265, a third MOS transistor 266 and a fourth MOS transistor 269; the positive output end of the first transconductance amplifier 290 is connected to a drain electrode of the first MOS transistor 262 through the fifth switch 261, the drain electrode of the first MOS transistor 262 is connected to a gate electrode of the first MOS transistor 262, the gate electrode of the first MOS transistor 262 is connected to a gate electrode of the second MOS transistor 265 through the sixth switch 263, a source electrode of the first MOS transistor 262 is connected to a source electrode of the second MOS transistor 265, the gate electrode of the second MOS transistor 265 is connected to the source electrode of the second MOS transistor 265 through the first capacitor 264, a drain electrode of the second MOS transistor 265 is connected to a drain electrode of the third MOS transistor 266 through the photoelectric conversion circuit 100, a gate electrode of the third MOS transistor 266 is connected to a source electrode of the third MOS transistor 266 through the second capacitor 267, the gate electrode of the third MOS transistor 266 is connected to a gate electrode of the fourth MOS transistor 269 through the seventh switch 268, the source electrode of the third MOS transistor 266 is connected to a source electrode of the fourth MOS transistor 269, the gate electrode of the fourth MOS transistor 269 is connected to a drain electrode of the fourth MOS transistor 269, and the drain electrode of the fourth MOS transistor 269 is connected to the negative output end of the first transconductance amplifier 290 through the eighth switch 260.

When the fifth switch 261, the sixth switch 263, the seventh switch 268 and the eighth switch 260 are all turned on, the current sampling circuit 270 is configured to detect the signal remaining in the background optical signal; and when the fifth switch 261, the sixth switch 263, the seventh switch 268 and the eighth switch 260 are all turned off, the current sampling circuit 270 is configured to cancel the signal remaining in the background optical signal.

Specifically, the third switch 253 and the fourth switch 254 may be controlled to be turned on or turned off through a third control signal (shn), and the fifth switch 261, the sixth switch 263, the seventh switch 268, and the eighth switch 260 may be controlled to be turned on or turned off through a fourth control signal (shp).

More specifically, when shn=1 (at a high level), the third switch 253 and the fourth switch 254 are turned on, and when shn=0 (at a low level), the third switch 253 and the fourth switch 254 are turned off. Similarly, when shp=1 (at a high level), the fifth switch 261, the sixth switch 263, the seventh switch 268, and the eighth switch 260 are turned on, and when the shp=0 (at a low level), the fifth switch 261, the sixth switch 263, the seventh switch 268, and the eighth switch 260 are turned off.

In an actual operation, as shown in FIG. 5, when shp=1, shn=0, that is, when the third switch 253 and the fourth switch 254 are turned off and the fifth switch 261, the sixth switch 263, the seventh switch 268 and the eighth switch 260 are turned on, the first transconductance amplifier 290 forms the negative feedback loop with the first MOS transistor, the second MOS transistor 265, the third MOS transistor 266, the photoelectric conversion circuit 100, and the fourth MOS transistor 269; and according to a principle of virtual open of an amplifier, current may merely flow from a power supply to reference ground through a branch of the second MOS transistor 265, the photoelectric conversion circuit 100, and the third MOS transistor 266. At this time, the photoelectric conversion circuit 100 merely receives the background optical signal, and therefore, a current flowing through the second MOS transistor 265 and the third MOS transistor 266 is a current generated by the signal remaining in the background optical signal.

That is, it merely needs to make the current flowing through the second MOS transistor 265 and the third MOS transistor 266 when shp=0 and shn=1 equal to the current flowing through the second MOS transistor 265 and the third MOS transistor 266 when shp=1 and shn=0, and the differential signal conversion circuit 200 in the working state could cancel the signal remaining in the background optical signal in the current signal.

In other words, in the embodiment of the present disclosure, the negative feedback loop may be added to the differential signal conversion circuit 200 to cancel the current of the background optical signal in an input current, thereby increasing the dynamic range of the valid signal input by the differential signal conversion circuit 200.

Those skilled in the art shall understand that a MOS transistor is also referred to as a metal-oxide-semiconductor field-effect transistor (Metal-Oxide-Semiconductor Field-Effect Transistor, MOSFET). The MOSFET can be divided into an "N-type" MOS transistor (NMOSFET) and a "P-type" MOS transistor (PMOSFET) according to a polarity of a "channel" (a working carrier); and for the NMOSFET, a source electrode and a drain electrode thereof are connected to a N-type semiconductor, a drain end is connected to a high voltage, a source end is connected to a low voltage, and the current actually flows in the drain electrode. For the PMOSFET, a source electrode and a drain electrode thereof are connected to a P-type semiconductor, a source end is connected to a high voltage, a drain end is connected to a low voltage, and the current actually flows out the drain electrode. In the embodiment of the present disclosure, the first MOS transistor 262 and the second MOS transistor 265 may be the "N-type" MOS transistor, and the third MOS transistor 266 and the fourth MOS transistor 269 may be the "P-type" MOS transistor. However, the embodiment of the present disclosure is not limited thereto.

It should also be understood that in the embodiment of the present disclosure, the negative feedback loop composed of the third switch 253, the fourth switch 254, and the current sampling circuit 270 is intended to increase the dynamic range of the valid signal input by the differential signal conversion circuit 200. That is, a circuit structure as shown in FIG. 2 is merely an exemplary description, and the embodiment of the present disclosure is not specifically limited.

In addition, since the input end of the first transconductance amplifier 290 has a fixed first voltage, if the voltage of the Vipi is too high, a linear region of a tail current source in the first transconductance amplifier 290 is overwhelmed, which leads to an abnormal operation of the differential signal conversion circuit 200.

Therefore, further, in order to ensure that the differential signal conversion circuit 200 is in a normal operating state, optionally, as shown in FIG. 2, the differential signal conversion circuit 200 includes: a second transconductance amplifier 280, a positive input end of the second transconductance amplifier 280 is connected to the positive input end of the first transconductance amplifier 290, a negative input end of the second transconductance amplifier 280 receives a common mode voltage, and the common mode voltage is used for stabilizing a voltage value of the positive input end of the first transconductance amplifier 290.

Specifically, as shown in FIG. 2, a second transconductance amplifier 280 is added to the current sampling circuit 270 to form another negative feedback loop; and according to "a virtual short principle", a voltage at the positive input end of the first transconductance amplifier 290 is equal to a voltage at a positive input end of the second transconductance amplifier 280, thereby limiting a voltage of the Vipi to a certain common mode voltage Vcm. Furthermore, the differential signal conversion circuit 200 can be ensured to be in a normal operation state by controlling the common mode voltage Vcm.

In summary, in the embodiment of the present disclosure, the differential signal conversion circuit 200 can suppress the common mode noise introduced from the ambient by inputting the differential current signal and outputting the differential signals of the two phases. Further, by inputting the first voltage (for example, a positive offset voltage) to the first transconductance amplifier 290, the signal-to-noise ratio of the output signal can be further improved. Further, the dynamic range of the valid signal input by the differential signal conversion circuit 200 can be increased through the current sampling circuit 270. The differential signal conversion circuit 200 can be ensured to be in a normal operating state through the second transconductance amplifier 280.

It should be understood that the negative feedback loop formed by the current sampling circuit 270 and the second transconductance amplifier 280 belongs to an auxiliary circuit of the differential signal conversion circuit 200, and in an actual application process, the circuit can be laid out according to actual requirements, which is not specifically limited in the embodiment of the present disclosure.

The subtraction amplifier 300 according to an embodiment of the present disclosure will be described by way of example.

Figure 3:
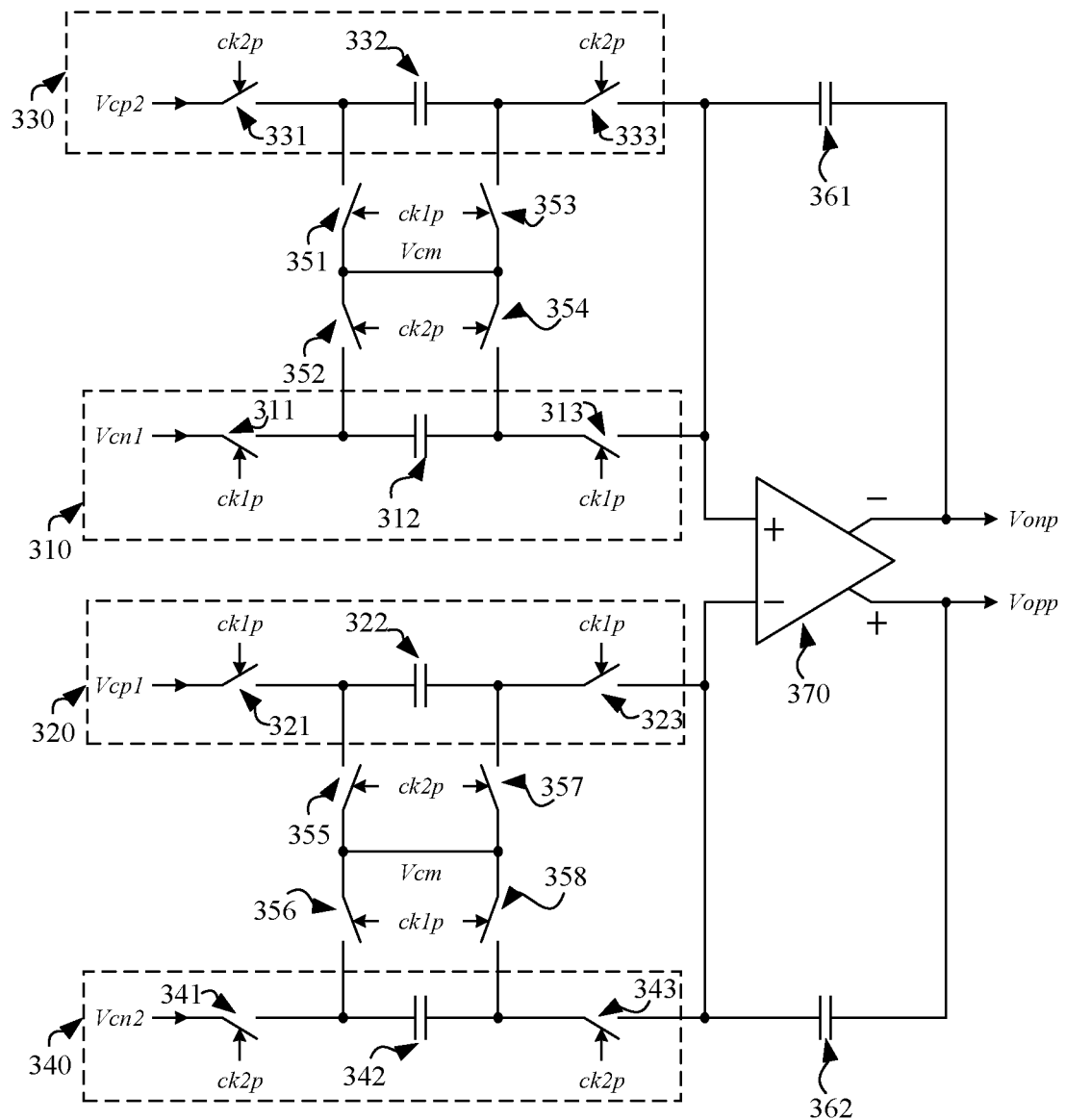
FIG. 3 is a schematic diagram of a subtraction amplifier of an embodiment of the present disclosure.

FIG. 3 is a schematic diagram of a subtraction amplifier 300 of an embodiment of the present disclosure.

As shown in FIG. 3, the subtraction amplifier 300 includes: a first branch 310, a second branch 320, a third branch 330, a fourth branch 340 and a third transconductance amplifier 370, where the first branch 310 and the second branch 320 are configured to receive the first differential signal, the third branch 330 and the fourth branch 340 are configured to receive the second differential signal, and the third transconductance amplifier 370 is configured to generate the third differential signal according to the first differential signal and the second differential signal.

Specifically, as shown in FIG. 3, the first branch 310 includes a thirteenth switch 311, a seventh capacitor 312, and a fourteenth switch 313; the second branch 320 includes a fifteenth switch 321 and an eighth capacitor 322, and a sixteenth switch 323; the third branch 330 includes a seventeenth switch 331, a ninth capacitor 332 and a seventeenth switch 333; and the fourth branch 340 includes an eighteenth switch 341, a tenth capacitor 342 and a nineteen switch 343. As shown in FIG. 3, one end of the ninth capacitor 332 is connected to one end of the seventh capacitor 312 through the twentieth switch 351 and the twenty-first switch 352 in sequence, and the other end of the ninth capacitor 332 is connected to the other end of the seventh capacitor 312 through the twenty-second switch 353 and the twenty-third switch 354 in sequence; and one end of the eighth capacitor 322 is connected to one end of the tenth capacitor 342 through the twenty-fourth switch 355 and the twenty-fifth switch 356 in sequence, and the other end of the eighth capacitor 322 is connected to the other end of the tenth capacitor 342 through the twenty-sixth switch 357 and the twenty-seventh switch 358 in sequence.

Further, a positive input end of the third transconductance amplifier 370 is connected to a negative output end of the third transconductance amplifier 370 through an eleventh capacitor 361, and a negative input end of the third transconductance amplifier 370 is connected to a positive output end of the third transconductance amplifier 370 through a twelfth capacitor 362.

A fifth control signal (ck1$p$) is used to control on and off of the following switches the thirteenth switch 311, the fourteenth switch 313, the fifteenth switch 321, the sixteenth switch 323, the twentieth switch 351, the twenty-second switch 353, the twenty-fifth switch 356, and the twenty-seventh switch 358.

In addition, a sixth control signal (ck2$p$) is used to control on and off of the following switches the seventeenth switch 331, the seventeenth switch 333, the eighteenth switch 341, the nineteenth switch 343, the twenty-first switch 352, the twenty-third switch 354, the twenty-fourth switch 355, and the twenty-sixth switch 357.

In the embodiment of the present disclosure, in combination with a conversion process of the differential signal conversion circuit 200, a main function of the subtraction amplifier 300 is to subtract the second differential signal from the first differential signal that are output by the differential signal conversion circuit 200 and amplify to obtain a third differential signal, and then the third differential signal is output. Thus, conversion of the current signal is achieved.

Specifically, when the fifth control signal ck1$p$=1 (at a high level), the corresponding switches are controlled to be turned on, and when the fifth control signal ck1$p$=0 (at a low level), the corresponding switches are controlled to be turned off; similarly, when the sixth control signal ck2$p$=1 (at a high level), the corresponding switches are controlled to be turned on, and when the sixth control signal ck2$p$=0 (at a low level), the corresponding switches are controlled to be turned off.

It is assumed that Cfp=Cfn=Cf, Csp1=Csp2=Csn1=Csn2=Cs, where the Cfp denotes a capacitance value of the eleventh capacitor 361, the Cfn denotes a capacitance value of the twelfth capacitor 362, and the Csp1, Csn1, Csp2, and Csn2 respectively denote a capacitance value of the seventh capacitor 312, a capacitance value of the eighth capacitor 322, a capacitance value of the ninth capacitor 332 and a capacitance value of the tenth capacitor 342.

As shown in FIG. 5, in the actual operation, the first switch 251 and the second switch 252 are turned off. When ck1$i$=1, ck2$i$=0, ck1$p$=1, and ck2$p$=0, the first differential signal is converted and stored in the eleventh capacitor 361 and the twelfth capacitor 362, and at this time, an output of the subtraction amplifier 300 may be expressed as: Vo,pga(1/2)=Vopp(1/2)−Vonp(1/2)=Cs/Cf(Vcp1−Vcn1), where Cs/Cf is an amplification factor, and Vcp1−Vcn1 is the first differential signal of the embodiment of the present disclosure. When ck1$i$=0, ck2$i$=1, ck1$p$=0, and ck2$p$=1, an output of the subtraction amplifier 300 may be expressed as: Vo,pga(1)=Cs/Cf [(Vcp1−Vcn1)−(Vcp2−Vcn2)], where Vcp2−Vcn2 is the second differential signal of the embodiment of the present disclosure.

By analogy, after clock periods N, an output of the subtraction amplifier 300 may be expressed as: Vo,pga(N)=N*(Cs/Cf)*[(Vcp1−Vcn1)−(Vcp2−Vcn2)]. As a result, a difference value between the first differential signal and the second differential signal is amplified through the subtraction amplifier 300, thereby demodulating the useful optical signal and the modulated optical signal.

It should be understood that a circuit structure as shown in FIG. 3 is merely an example of the subtraction amplifier 300 of the embodiment of the present disclosure, and the embodiment of the present disclosure is not limited thereto.

Figure 4:
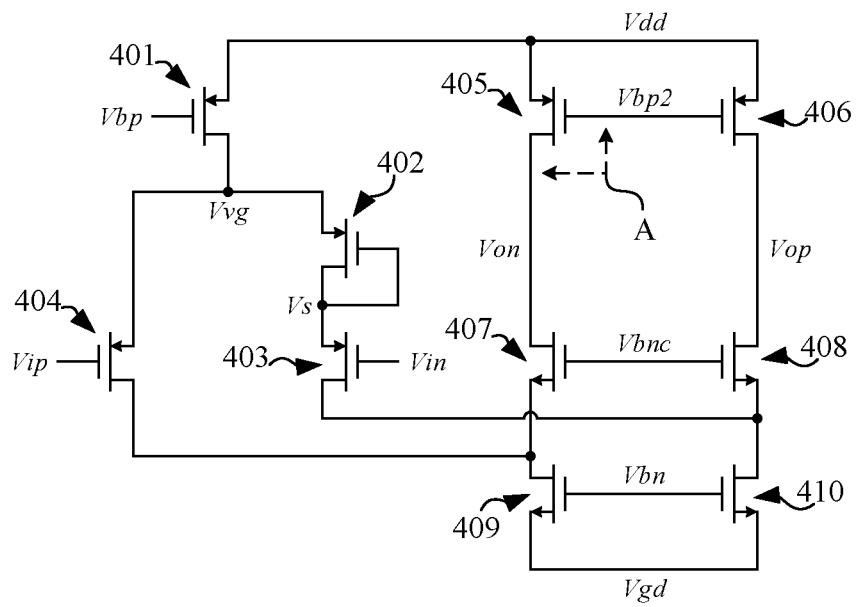
FIG. 4 is a schematic diagram of a transconductance amplifier of an embodiment of the present disclosure.

FIG. 4 is a schematic diagram of a first transconductance amplifier 290 of an embodiment of the present disclosure.

As shown in FIG. 4, a fifth MOS transistor 403 and a sixth MOS transistor 404 constitute a differential inputting pair transistor for providing a required quantity of transconductance, and a seventh MOS transistor 401 is a tail current source of the inputting pair transistor for providing a certain bias current. A self-cascode MOSFET (Self-Cascode MOSFET, SCM) composed of an eighth MOS transistor 407, a ninth MOS transistor 408, a tenth MOS transistor 409, and an eleventh MOS transistor 410 is configured to receive a current output by the differential inputting pair transistor and provide a certain output load resistance. For example, the self-cascode MOS transistor in the embodiment of the present disclosure may include two PMOSFETs, and when one of the PMOSFETs operates in a linear region, it may be equivalent to a resistor in an electrical characteristic.

In addition, a current mirror formed by a twelfth MOS transistor 405 and a thirteenth MOS transistor 406 also provides a certain output load resistor, the resistor is connected in parallel with the equivalent resistor of the self-cascode MOS transistor to jointly form an output resistance of the transconductance amplifier.

As shown in FIG. 4, a fourteenth MOS transistor 402 is disposed between nodes Vvg and Vs, and when the first transconductance amplifier 290 operates normally, a current flowing through the fifth MOS transistor 403 is basically equal to a current flowing through the sixth MOS transistor 404, and in order to ensure that the two currents are equal, Vip−Vvg=Vin−Vs is necessarily satisfied, that is, Vip−Vin=Vvg−Vs. Thus, the first transconductance amplifier 290 generates a constant first voltage.

It should be understood that a circuit structure of the first transconductance amplifier 290 as shown in FIG. 4 may also adopt a circuit structure of a transconductance amplifier in the prior art. That is, the first transconductance amplifier 290 in the embodiment of the present disclosure may be any circuit structure capable of generating a constant first voltage.

It should also be understood that a function of the second transconductance amplifier 280 of the embodiment of the present disclosure is: and a function of the third transconductance amplifier 370 is:, and the circuit structure of the embodiment of the present disclosure is not specifically limited.

For example, for the second transconductance amplifier 280, on the basis of the first transconductance amplifier 290 as shown in FIG. 4, Vvg and Vs may be short-circuited and the fourteenth MOS transistor 402 may be removed, and Vbp2 and Von may be short-circuited, and Vbp2 may no longer be connected to a bias voltage.

For another example, for the third transconductance amplifier 370, on the basis of the first transconductance amplifier 290 shown in FIG. 4, Vvg and Vs may be short-circuited and the fourteenth MOS transistor 402 may be removed.

Finally, it should be noted that the circuit in the embodiment of the present disclosure may also include: a reset circuit and a negative feedback loop, such that an initial state of a capacitance involved in the embodiment of the present disclosure is 0, and the output common mode voltage is Vcm. Since the reset circuit and the common mode negative feedback loop outputting by means of differential are not critical to the present disclosure, they will not be described redundantly herein. It should also be understood that the circuit in the embodiment of the present disclosure may also include: an analog-to-digital converter connected to the signal conversion circuit of the embodiment of the present disclosure for converting an analog signal output by the signal conversion circuit into a digital signal.

In addition, a heart rate sensor including the foregoing signal conversion circuit is also provided in an embodiment of the present disclosure. Optionally, the heart rate sensor may also include: an analog to digital converter, connected to the signal conversion circuit, and configured to convert an analog signal output by the signal conversion circuit into a digital signal. Further, it may also include a data processing circuit connected to the digital-to-analog converter for receiving and processing the digital signal.

In an embodiment of the disclosure, an electronic device including the foregoing heart rate sensor is also provided. It should be understood that the electronic device may be any electronic device, for example, the electronic device may be an intelligent wearable device such as an earphone, a wristband or the like; for another example, the electronic device is a mobile phone, a tablet computer, a notebook computer, a computer, an MP3, an MP4, or the like.

It should also be noted that, terms used in embodiment of the present disclosure and the claims appended hereto are merely for the purpose of describing particular embodiments, and are not intended to limit the embodiments of the present disclosure.

For example, the use of a singular form of "a", "the" and "said" in the embodiment of the present disclosure and the claims appended hereto are also intended to include a plural form, unless otherwise clearly indicated herein by context.

Persons of ordinary skill in the art may be aware that, various exemplary units described in conjunction with the embodiments disclosed herein may be implemented by electronic hardware or a combination of computer software and electronic hardware. Whether these functions are executed in hardware or software mode depends on a particular application and a design constraint condition of the technical solution. Persons skilled in the art may use different methods to implement the described functions for every particular application, but it should not be considered that such implementation goes beyond the scope of the present disclosure.

Persons skilled in the art may clearly understand that the apparatus and units described may or may not be physically separated for clarity and brevity. A part of or all of the units may be selected according to actual demands to achieve objectives of the embodiments of the present disclosure.

The foregoing contents are merely a specific implementation of the embodiments of the present disclosure, but the protection scope of the present disclosure is not limited thereto. Various modifications or replacements may be readily conceivable to any person skilled in the art within the technical scope disclosed in the present disclosure, and such modifications or replacements shall fall within the protection scope of the present disclosure. Therefore, the protection scope of the embodiments the present disclosure shall be defined by the claims.

What is claimed is:

1. A signal conversion circuit, comprising:
   a photoelectric conversion circuit, configured to convert an optical signal into a current signal, wherein the current signal in a first phase comprises a signal converted from a useful optical signal, a modulated optical signal and a background optical signal in the optical signal, and the current signal in a second phase comprises a signal converted from the background optical signal, the useful optical signal is an optical signal carrying target information;
   a differential signal conversion circuit, connected to the photoelectric conversion circuit, and configured to convert the current signal into a first differential signal and a second differential signal, wherein the first differential signal is an integration signal of the current signal in the first phase, and the second differential signal is an integration signal of the current signal in the second phase; and
   a subtraction amplifier, connected to the differential signal conversion circuit, and configured to subtract the second differential signal from the first differential signal and amplify an obtained difference value to generate a third differential signal;
   wherein the differential signal conversion circuit comprises a first differential signal generation circuit configured to integrate the current signal in the first phase; and a second differential signal generation circuit configured to integrate the current signal in the second phase, wherein the first differential signal generation circuit is connected in parallel with the second differential signal generation circuit;
   the first differential signal generation circuit comprises a first integration circuit and a second integration circuit, the second differential signal generation circuit comprises a third integration circuit and a fourth integration circuit, each of integration circuits comprises a capacitor and a switch, and the differential signal conversion circuit further comprises a first switch, a second switch, and a first transconductance amplifier, one end of the photoelectric conversion circuit is connected to a positive input end of the first transconductance amplifier through the first switch, and the other end of the photoelectric conversion circuit is connected to a negative input end of the first transconductance amplifier through the second switch, the positive input end of the first transconductance amplifier is connected to a negative output end of the first transconductance amplifier through the first integration circuit, the negative input end of the first transconductance amplifier is connected to a positive output end of the first transconductance amplifier through the second integration circuit, the third integration circuit is connected in parallel with the first integration circuit, and the fourth integration circuit is connected in parallel with the second integration circuit.

2. The signal conversion circuit according to claim 1, wherein:
   when both the first switch and the second switch are turned on, the first integration circuit and the second integration circuit integrate the current signal in the first phase, and the third integration circuit and the fourth integration circuit integrate the current signal in the second phase.

3. The signal conversion circuit according to claim 2, wherein:
the photoelectric conversion circuit is a photodiode, the first transconductance amplifier is connected to a first voltage, and the first voltage is used for adjusting a reverse bias voltage of the photodiode.

4. The signal conversion circuit according to claim 3, wherein:
the differential signal conversion circuit further comprises a second transconductance amplifier, a positive input end of the second transconductance amplifier is connected to the positive input end of the first transconductance amplifier, a negative input end of the second transconductance amplifier receives a common mode voltage, and the common mode voltage is used for stabilizing a voltage value of the positive input end of the first transconductance amplifier.

5. The signal conversion circuit according to claim 2, wherein:
the differential signal conversion circuit further comprises a second transconductance amplifier, a positive input end of the second transconductance amplifier is connected to the positive input end of the first transconductance amplifier, a negative input end of the second transconductance amplifier receives a common mode voltage, and the common mode voltage is used for stabilizing a voltage value of the positive input end of the first transconductance amplifier.

6. The signal conversion circuit according to claim 1, wherein:
the photoelectric conversion circuit is a photodiode, the first transconductance amplifier is connected to a first voltage, and the first voltage is used for adjusting a reverse bias voltage of the photodiode.

7. The signal conversion circuit according to claim 6, wherein:
the differential signal conversion circuit further comprises a second transconductance amplifier, a positive input end of the second transconductance amplifier is connected to the positive input end of the first transconductance amplifier, a negative input end of the second transconductance amplifier receives a common mode voltage, and the common mode voltage is used for stabilizing a voltage value of the positive input end of the first transconductance amplifier.

8. The signal conversion circuit according to claim 1, wherein:
the differential signal conversion circuit comprises a negative feedback loop configured to cancel a signal remaining in the background optical signal when the differential signal conversion circuit converts the current signal into the first differential signal and the second differential signal.

9. The signal conversion circuit according to claim 8, wherein:
the differential signal conversion circuit further comprises a second transconductance amplifier, a positive input end of the second transconductance amplifier is connected to the positive input end of the first transconductance amplifier, a negative input end of the second transconductance amplifier receives a common mode voltage, and the common mode voltage is used for stabilizing a voltage value of the positive input end of the first transconductance amplifier.

10. The signal conversion circuit according to claim 8, wherein:
the negative feedback loop comprises a third switch, a fourth switch, and a current sampling circuit, the first integration circuit is connected to the negative output end of the first transconductance amplifier through the third switch, the second integration circuit is connected to the positive output end of the first transconductance amplifier through the fourth switch, and the positive output end of the first transconductance amplifier is connected to the negative output end of the first transconductance amplifier through the current sampling circuit;
wherein when both the third switch and the fourth switch are turned off, the current sampling circuit is configured to detect the signal remaining in the background optical signal; and when both the third switch and the fourth switch are turned on, the current sampling circuit is configured to cancel the signal remaining in the background optical signal.

11. The signal conversion circuit according to claim 10, wherein:
the differential signal conversion circuit further comprises a second transconductance amplifier, a positive input end of the second transconductance amplifier is connected to the positive input end of the first transconductance amplifier, a negative input end of the second transconductance amplifier receives a common mode voltage, and the common mode voltage is used for stabilizing a voltage value of the positive input end of the first transconductance amplifier.

12. The signal conversion circuit according to claim 10, wherein:
the current sampling circuit comprises a fifth switch, a sixth switch, a seventh switch, an eighth switch, a first capacitor, a second capacitor, a first metal-oxide-semiconductor (MOS) transistor, a second MOS transistor, a third MOS transistor and a fourth MOS transistor;
the positive output end of the first transconductance amplifier is connected to a drain electrode of the first MOS transistor through the fifth switch, the drain electrode of the first MOS transistor is connected to a gate electrode of the first MOS transistor, a gate electrode of the gate electrode of the first MOS transistor is connected to a gate electrode of the second MOS transistor through the sixth switch, a source electrode of the first MOS transistor is connected to a source electrode of the second MOS transistor, the gate electrode of the second MOS transistor is connected to the source electrode of the second MOS transistor through the first capacitor, a drain electrode of the second MOS transistor is connected to a drain electrode of the third MOS transistor through the photoelectric conversion circuit, a gate electrode of the third MOS transistor is connected to a source electrode of the third MOS transistor through the second capacitor, the gate electrode of the third MOS transistor is connected to a gate electrode of the fourth MOS transistor through the seventh switch, the source electrode of the third MOS transistor is connected to a source electrode of the fourth MOS transistor, the gate electrode of the fourth MOS transistor is connected to a drain electrode of the fourth MOS transistor, and the drain electrode of the fourth MOS transistor is connected to the negative output end of the first transconductance amplifier through the eighth switch.

13. The signal conversion circuit according to claim 12, wherein:
the differential signal conversion circuit further comprises a second transconductance amplifier, a positive input end of the second transconductance amplifier is connected to the positive input end of the first transconductance amplifier, a negative input end of the second transconductance amplifier receives a common mode voltage, and the common mode voltage is used for stabilizing a voltage value of the positive input end of the first transconductance amplifier.

14. The signal conversion circuit according to claim 12, wherein:
when the fifth switch, the sixth switch, the seventh switch, and the eighth switch are all turned on, the current sampling circuit is configured to detect the signal remaining in the background optical signal; and when the fifth switch, the sixth switch, the seventh switch and the eighth switch are all turned off, the current sampling circuit is configured to cancel the signal remaining in the background optical signal.

15. The signal conversion circuit according to claim 14, wherein:
the differential signal conversion circuit further comprises a second transconductance amplifier, a positive input end of the second transconductance amplifier is connected to the positive input end of the first transconductance amplifier, a negative input end of the second transconductance amplifier receives a common mode voltage, and the common mode voltage is used for stabilizing a voltage value of the positive input end of the first transconductance amplifier.

16. The signal conversion circuit according to claim 1, wherein:
the differential signal conversion circuit further comprises a second transconductance amplifier, a positive input end of the second transconductance amplifier is connected to the positive input end of the first transconductance amplifier, a negative input end of the second transconductance amplifier receives a common mode voltage, and the common mode voltage is used for stabilizing a voltage value of the positive input end of the first transconductance amplifier.

17. The signal conversion circuit according to claim 1, wherein:
the subtraction amplifier comprises a first branch, a second branch, a third branch, a fourth branch and a third transconductance amplifier, wherein the first branch and the second branch are configured to receive the first differential signal, the third branch and the fourth branch are configured to receive the second differential signal, and the third transconductance amplifier is configured to generate the third differential signal according to the first differential signal and the second differential signal.

18. A heart rate sensor, comprising a signal conversion circuit, wherein the signal conversion circuit comprises:
a photoelectric conversion circuit, configured to convert an optical signal into a current signal, wherein the current signal in a first phase comprises a signal converted from a useful optical signal, a modulated optical signal and a background optical signal in the optical signal, and the current signal in a second phase comprises a signal converted from the background optical signal, the useful optical signal is an optical signal carrying target information;
a differential signal conversion circuit, connected to the photoelectric conversion circuit, and configured to convert the current signal into a first differential signal and a second differential signal, wherein the first differential signal is an integration signal of the current signal in the first phase, and the second differential signal is an integration signal of the current signal in the second phase; and
a subtraction amplifier, connected to the differential signal conversion circuit, and configured to subtract the second differential signal from the first differential signal and amplify an obtained difference value to generate a third differential signal;
wherein the differential signal conversion circuit comprises a first differential signal generation circuit configured to integrate the current signal in the first phase; and a second differential signal generation circuit configured to integrate the current signal in the second phase, wherein the first differential signal generation circuit is connected in parallel with the second differential signal generation circuit;
the first differential signal generation circuit comprises a first integration circuit and a second integration circuit, the second differential signal generation circuit comprises a third integration circuit and a fourth integration circuit, each of integration circuits comprises a capacitor and a switch, and the differential signal conversion circuit further comprises a first switch, a second switch, and a first transconductance amplifier, one end of the photoelectric conversion circuit is connected to a positive input end of the first transconductance amplifier through the first switch, and the other end of the photoelectric conversion circuit is connected to a negative input end of the first transconductance amplifier through the second switch, the positive input end of the first transconductance amplifier is connected to a negative output end of the first transconductance amplifier through the first integration circuit, the negative input end of the first transconductance amplifier is connected to a positive output end of the first transconductance amplifier through the second integration circuit, the third integration circuit is connected in parallel with the first integration circuit, and the fourth integration circuit is connected in parallel with the second integration circuit.

* * * * *